US011173314B2

(12) United States Patent
Ollivier

(10) Patent No.: US 11,173,314 B2
(45) Date of Patent: Nov. 16, 2021

(54) IMPLANTABLE LEAD

(71) Applicant: SORIN CRM SAS, Clamart (FR)

(72) Inventor: Jean-Francois Ollivier, Gif sur Yvette (FR)

(73) Assignee: Sorin CRM SAS, Clamart (FR)

( * ) Notice: Subject to any disclaimer, the term of this patent is extended or adjusted under 35 U.S.C. 154(b) by 232 days.

(21) Appl. No.: 16/130,830

(22) Filed: Sep. 13, 2018

(65) Prior Publication Data
US 2019/0083792 A1 Mar. 21, 2019

(30) Foreign Application Priority Data

Sep. 20, 2017 (EP) ..................................... 17306230

(51) Int. Cl.
*A61N 1/375* (2006.01)
*A61N 1/05* (2006.01)

(52) U.S. Cl.
CPC ......... *A61N 1/3752* (2013.01); *A61N 1/0563* (2013.01); *A61N 1/37512* (2017.08)

(58) Field of Classification Search
CPC . A61N 1/3752; A61N 1/37512; A61N 1/0563
See application file for complete search history.

(56) References Cited

U.S. PATENT DOCUMENTS

| | | | | |
|---|---|---|---|---|
| 4,481,953 A | * | 11/1984 | Gold ...................... | A61N 1/056 600/374 |
| 5,050,601 A | * | 9/1991 | Kupersmith ......... | A61N 1/0563 607/122 |
| 5,174,288 A | * | 12/1992 | Bardy .................. | A61N 1/0563 607/2 |
| 5,303,704 A | | 4/1994 | Molacek et al. | |
| 5,871,530 A | * | 2/1999 | Williams ............. | A61N 1/0563 607/122 |
| 5,919,222 A | * | 7/1999 | Hjelle .................. | A61N 1/0563 600/374 |

(Continued)

FOREIGN PATENT DOCUMENTS

| | | |
|---|---|---|
| EP | 2 559 453 A1 | 2/2013 |
| EP | 1 641 084 B1 | 9/2013 |

(Continued)

OTHER PUBLICATIONS

Search Report on European Patent Application No. 17306230.8 dated Feb. 12, 2018. 4 pages.

(Continued)

*Primary Examiner* — John R Downey
(74) *Attorney, Agent, or Firm* — Foley & Lardner LLP

(57) ABSTRACT

The present disclosure relates to an implantable lead comprising an elongated lead body having at least one lumen therein and at least one through hole, and at least one electrically conductive wire. For at least one of said at least one lumen, a first through hole extends from an outer surface of the lead body into said lumen, and an electrically conductive wire is arranged in said lumen at least on one side of said first through hole. Furthermore, said electrically conductive wire is further arranged in a configuration exiting the lumen via said first through hole and wound around a predefined portion of the outer surface of the lead body.

18 Claims, 3 Drawing Sheets

(56) References Cited

U.S. PATENT DOCUMENTS

| | | | | |
|---|---|---|---|---|
| 5,928,277 | A * | 7/1999 | Laske | A61N 1/0563 607/122 |
| 8,523,588 | B2 * | 9/2013 | Forslund | A61N 1/056 439/289 |
| 2002/0095202 | A1 * | 7/2002 | Schmidt | A61B 5/0422 607/122 |
| 2003/0217463 | A1 * | 11/2003 | Schmidt | A61N 1/05 29/857 |
| 2006/0161236 | A1 * | 7/2006 | King | A61N 1/0553 607/117 |
| 2006/0206153 | A1 * | 9/2006 | Libbus | A61N 1/0551 607/9 |
| 2008/0161871 | A1 * | 7/2008 | Knapp | A61N 1/056 607/5 |
| 2010/0042169 | A1 * | 2/2010 | Barker | H01R 13/621 607/2 |
| 2011/0004286 | A1 * | 1/2011 | Olson | A61N 1/056 607/122 |
| 2011/0106231 | A1 * | 5/2011 | Doan | A61N 1/056 607/116 |
| 2011/0160785 | A1 * | 6/2011 | Mori | A61N 1/0563 607/5 |
| 2014/0207149 | A1 * | 7/2014 | Hastings | A61N 1/0587 606/129 |
| 2014/0330325 | A1 * | 11/2014 | Thompson-Nauman | A61N 1/39622 607/4 |
| 2015/0297884 | A1 * | 10/2015 | Jang | A61N 1/056 607/119 |
| 2015/0328460 | A1 * | 11/2015 | Greiner | A61N 1/0551 607/46 |
| 2016/0022990 | A1 * | 1/2016 | Risi | A61N 1/0541 607/57 |
| 2016/0296749 | A1 * | 10/2016 | Farr | H01R 43/16 |
| 2017/0001001 | A1 * | 1/2017 | Liu | A61N 1/056 |
| 2018/0289968 | A1 * | 10/2018 | Lopez | A61N 1/36071 |

FOREIGN PATENT DOCUMENTS

| | | |
|---|---|---|
| EP | 2 664 354 A1 | 11/2013 |
| WO | WO-98/48887 A1 | 11/1998 |

OTHER PUBLICATIONS

Examination report issued in EP application No. 17306230.8 dated Apr. 6, 2020. 4 pages.

* cited by examiner

IMPLANTABLE LEAD

CROSS-REFERENCE TO RELATED PATENT APPLICATIONS

This application claims the benefit of and priority to European Application No. 17306230.8, filed Sep. 20, 2017, which is incorporated herein by reference in its entirety.

BACKGROUND

The present disclosure relates to the field of active medical implantable devices, such as implantable pacemakers and/or defibrillators. The present disclosure relates, in particular, to an implantable lead comprising an elongated tubular body with at least one lumen, and at least one electrically conductive wire.

Implantable leads for active implantable medical devices such as an implantable pacemaker and/or defibrillator typically comprise an elongated lead body, a proximal end configured to be plugged into a dedicated socket of the housing of the active implantable medical device, and a distal end configured for sensing and/or stimulating a tissue.

Typically, the proximal end of implantable leads comprises a pluggable electrical connector, which is usually configured according to standards of the art. For instance, it can be configured as a standard IS-1 or DF-1 connector, like in EP 1 641 084 B1, or following more recent developments, as a standard IS-4 or DF-4 connector. In the latter standards, an electrical connector member at the proximal end of the lead comprises a series of three electrically conductive rings spaced apart from one another in the longitudinal direction of the connector, and an axial contact pin protruding from the free or proximal end of the connector member. Typically, the rings and pin are dedicated to low voltage lines in leads destined for stimulation, such as leads using a standard IS-4 connector. In contrast, in leads destined also for defibrillation, such as leads using a standard DF-4 connector, two electrically conductive rings are dedicated to high voltage lines, while the third electrically conductive ring and the axial contact pin are dedicated to low voltage lines.

In turn, the distal end of known implantable leads usually comprises a series of sensing and/or stimulating electrodes connected, at least in the case of the IS-4 or DF-4 standards, to a respective one of the rings of the pluggable electrical connector via a respective electrically conductive line arranged in at least one lumen of the lead body. In known lead bodies of the multi-lumen type, which are often used in combination with the DF-4 standard, each electrically conductive line is arranged in a respective (secondary) lumen extending parallel to a main lumen of the lead body. Another electrically conductive line can be linked to the axial pin, which is usually accommodated in the proximal end of the main lumen and protrudes from the proximal end of the implantable lead through the connector member and is configured to be pluggable according to the desired standard.

A drawback of known implantable leads, in particular of the DF-4 type using a multi-lumen lead body, is that the portion of the lead body emerging from the electrical connector member is regularly submitted to intensive mechanical stress, in particular bending stress, occurring upon a doctor's manipulation during the implantation procedure, as well as during everyday movements of a patient with an implanted device. This mechanical stress applied especially at the level of the lead body emerging from the connector member can damage the lead body and especially the electrically conductive lines therein, resulting in a possible break of the same due to mechanical fatigue. Other areas of a lead body may also be submitted to bending stress, for instance parts of the lead disposed in a cavity of the heart (e.g. atrium or ventricle).

In the particular case of leads used also for defibrillation purposes, such as the DF-4 type, it is known to use micro-cables to realize the various electrical lines in a multi-lumen lead body as described above. Typically, these micro-cables can be flexible elements having a diameter of at most 2 French (0.66 mm), as described, for instance, in EP 2 559 453 A1 and EP 2 664 354 A1. Such micro-cables are also known to be resistant in tension but not so much in bending. Therefore, any area of the lead submitted to bending stress faces risks of a break of one or more of the micro-cables.

SUMMARY

In view of the above, an object of the present disclosure is to reduce the mechanical stress on the lead body and electrical conductive lines therein at areas of the lead body that may be submitted to bending stress, in particular at the area where the lead body emerges from the connector member, while still ensuring the necessary electrical connectivity.

The above-mentioned object is achieved with an implantable lead according to claim 1. The implantable lead comprises an elongated lead body having at least one lumen therein and at least one through hole, and at least one electrically conductive wire. For at least one of said at least one lumen, a first through hole extends from an outer surface of the lead body into said lumen, and an electrically conductive wire is arranged in said lumen at least on one side of said first through hole. Further, said electrically conductive wire is arranged in a configuration exiting the lumen via said first through hole and wound around a predefined portion of the outer surface of the lead body.

In the implantable lead, at least one electrically conductive wire is provided with a particular configuration. Before a predefined portion of the lead body, the wire is arranged within the lumen. Furthermore, at a through hole, which penetrates into the lumen from the outer surface of the lead body and defines the beginning of a predefined portion of the lead body, which is essentially a portion thereof of a predefined length, the electrically conductive wire exits the lumen and is then wound, essentially following a spiraling configuration, around the lead body over the predefined portion of the lead body. This configuration advantageously provides the electrically conductive wire with improved mechanical resistance and durability, especially against any mechanical stress, in particular any bending stress, over the length of the predefined portion. Advantageously, the predefined portion may be provided at areas of the lead body known to be subject to intense mechanical stress, in particular bending stress. Thus, in embodiments of an implantable lead comprising an electrical connector member, it is possible to provide the predefined portion as the portion of the lead body emerging from the distal end of the connector member. Furthermore, more than one such predefined portion may be provided along the lead to protect it at any other desired area also known to be subject to intense mechanical stress, in particular to bending, for instance, in the more distal sections of the lead typically disposed within a cavity of the heart.

In the present disclosure, it is to be understood that a "through hole" is distinct from a "lumen", a "lumen" being here understood essentially as a bore in the longitudinal direction of the lead body, which can be commonly an essentially tubular structure, and a "through hole" being here understood as an opening through the side wall of the lead body extending between the outer surface thereof and a lumen of the lead body. Furthermore, a lead body may have only one lumen, or a plurality of lumina, and one lumen may be centered or off-centered with respect to a main axis of the elongated lead body.

In addition, the terms "proximal" or "proximal end" of a device or structure will be used to refer to the direction or end of a structure intended to be facing towards the socket of the housing of an active medical implantable device, and the term "distal" or "distal end" will be used to refer to the opposite direction or end of a structure.

Further advantageous aspects and variants of the implantable lead are also described in the dependent claims and will become more evident in the following disclosure.

According to an embodiment, a second through hole, different from the first through hole, can extend from the outer surface of the lead body into one of said at least one lumen, and said electrically conductive wire can be arranged in a configuration entering said one of said at least one lumen via said second through hole. Thus, the electrically conductive wires can be made to re-enter a lumen after the wound configuration over the desired length of the predefined portion. This is advantageous, as it allows providing the predefined portion at any portion of the lead body.

According to a variant of an embodiment, said first through hole and said second through hole can extend into the same lumen, whereby said electrically conductive wire is arranged within the same lumen on either side of the predefined portion. Although preferred in some embodiments, this configuration is not intended to be limitative and provides the advantage that the same wire can be identified at both ends of an implantable lead, without confusion, especially in a multi-lumen lead body, as the lumen through which the at least one electrically conductive wire re-enters the lead body can be the same as the lumen in which the wire is arranged on the other side of the predefined portion.

According to a further variant of an embodiment, when the lead body has more than one lumen, said first through hole and said second through hole can extend into a different respective lumen, whereby said electrically conductive wire is arranged within a different lumen on either side of the predefined portion. This alternative or complementary configuration is also not limitative and provides the advantage of flexibility in the arrangement of the wires within a multi-lumen body, as the lumen through which the at least one electrically conductive wire re-enters the lead body does not need to be the same as the lumen in which the wire is arranged on the other side of the predefined portion.

According to an embodiment, first and/or second through holes can be spaced apart in a longitudinal direction of the lead body. In this way, it is possible to avoid creating a weakness point in the same section of the lead body by having too many through holes too close to one another.

According to an embodiment, first and/or second through holes can be offset with respect to each other in a circumferential direction of the lead body. In particular, first and/or second through holes could be offset in a circumferential direction of the lead body with respect to each other by 60° steps or multiples thereof. These configurations were found advantageous, as they facilitate the arrangement of wires, especially in a multi-lumen lead body. In these situations, without however being restricted thereto, these configurations were found advantageous in embodiments in which a wire does not need to re-enter the same lumen after the predefined portion.

According to an embodiment, said electrically conductive wire can be further arranged in a configuration wound at least once, in particular at least between one and six times, around the predefined portion of the outer surface of the lead body. This configuration was found advantageous, as winding electrically conductive wires over the larger diameter of the lead body and over the length of the predefined portion increases the resistance against breaking due to mechanical fatigue caused, in particular, by the bending stress to which the portion of the lead body emerging from a connector member is submitted during the lifetime of an implantable lead.

According to an embodiment, the lead body can be a multi-lumen lead body comprising a main lumen, and said at least one lumen can be different from the main lumen. For instance, one or more lumen provided with the first and/or second through holes can be arranged essentially parallel to the main lumen. In this case, it is understood that the "main" lumen does not need to be a "central" lumen and can, itself, be off-centered with respect to a main axis of the elongated lead body. In any case, with the present disclosure, it is possible to improve implantable leads using multi-lumen lead bodies. Since implantable leads using DF-4 standard connectors tend to use multi-lumen lead bodies, the present disclosure has the advantage that it is possible to provide higher resistance implantable leads having this standard connectivity.

According to an embodiment, said at least one electrically conductive wire can be a micro-cable. When applied to implantable leads used also for defibrillation purposes, for instance of the DF-4 type, the present disclosure advantageously provides protection against bending stress for micro-cables, which are otherwise known to be resistant in tension, but not in bending. In other words, with one or more predefined areas with the above-mentioned configuration of the electrically conductive wires, in the case of micro-cables, the present disclosure can provide an implantable lead having one or more areas presenting an improved resistance against bending stress.

According to an embodiment, the lead body can have a proximal end portion configured for connecting the implantable lead to a housing of an active medical implantable device, and a distal end potion configured for sensing and/or stimulating a tissue, and said first through hole and/or second through hole can be arranged closer to the proximal end portion than to the distal end portion. This configuration is preferred, as the predefined portion can, therefore, be a portion towards the proximal end of the lead body, in particular it can be a portion of the lead body within the connector member and/or a portion emerging from the same.

According to a variant of embodiment, the implantable lead can further comprise an electrical connector plug arranged at the proximal end portion of the lead body, and the predefined portion can be a portion of the lead body following the electrical connector plug, in particular, immediately following the electrical connector plug. As mentioned above, the present disclosure has the advantage of being applicable to implantable leads comprising a standardized connectivity and of providing an area with improved resistance to bending stress, in particular, immediately after the connector portion.

According to an embodiment, the implantable lead can further comprise at least one protective sleeve arranged over the lead body and extending at least over the predefined portion. This is advantageous, as it provides additional protection and stability while ensuring a necessary flexibility of the predefined portion, in particular against high mechanical stress such as high bending stress caused by a doctor during the manipulation and implantation of an implantable lead plugged to an active implantable medical device.

According to a variant of an embodiment, a distal end portion of the electrical connector plug can be arranged over a proximal end portion of the protective sleeve, whereby a portion of the protective sleeve is left uncovered by the electrical connector plug. The advantages relating to protection and mechanical stability and durability can, therefore, advantageously be extended to a portion within the connector member.

According to an embodiment, the implantable lead can further comprise an insulating sleeve arranged over the lead body and extending at least over the predefined portion, in particular, extending at least over the protective sleeve in a particular variant of an embodiment, more in particular, extending over the distal end portion of the electrical connector plug, and at least over the uncovered portion of the protective sleeve in a more particular variant of an embodiment. This is advantageous in order to ensure that body fluids do not filter in the predefined portion and/or in the connector member after a prolonged usage by a patient.

According to a variant of an embodiment, the protective sleeve and/or the insulating sleeve can be made of a flexible material, in particular a flexible biocompatible material. In this way, it is possible to customize the degree of flexibility, protection, mechanical stability and durability of the area covered by the sleeve(s) as desired.

BRIEF DESCRIPTION OF THE DRAWINGS

Additional features and advantages will be described hereafter with reference to the accompanying figures, wherein.

DETAILED DESCRIPTION

It is understood that the accompanying figures and the following description are intended to illustrate preferred embodiments of the disclosure, and that these embodiments do not necessarily represent the full scope of the disclosure.

In the following description, the same reference signs may be used to designate the same features throughout the figures illustrating a particular embodiment. Furthermore, similar reference signs may be used to designate the same or features realizing the same function in different embodiments, and the reader may be referred to a previous description for the sake of brevity.

Figure 1:
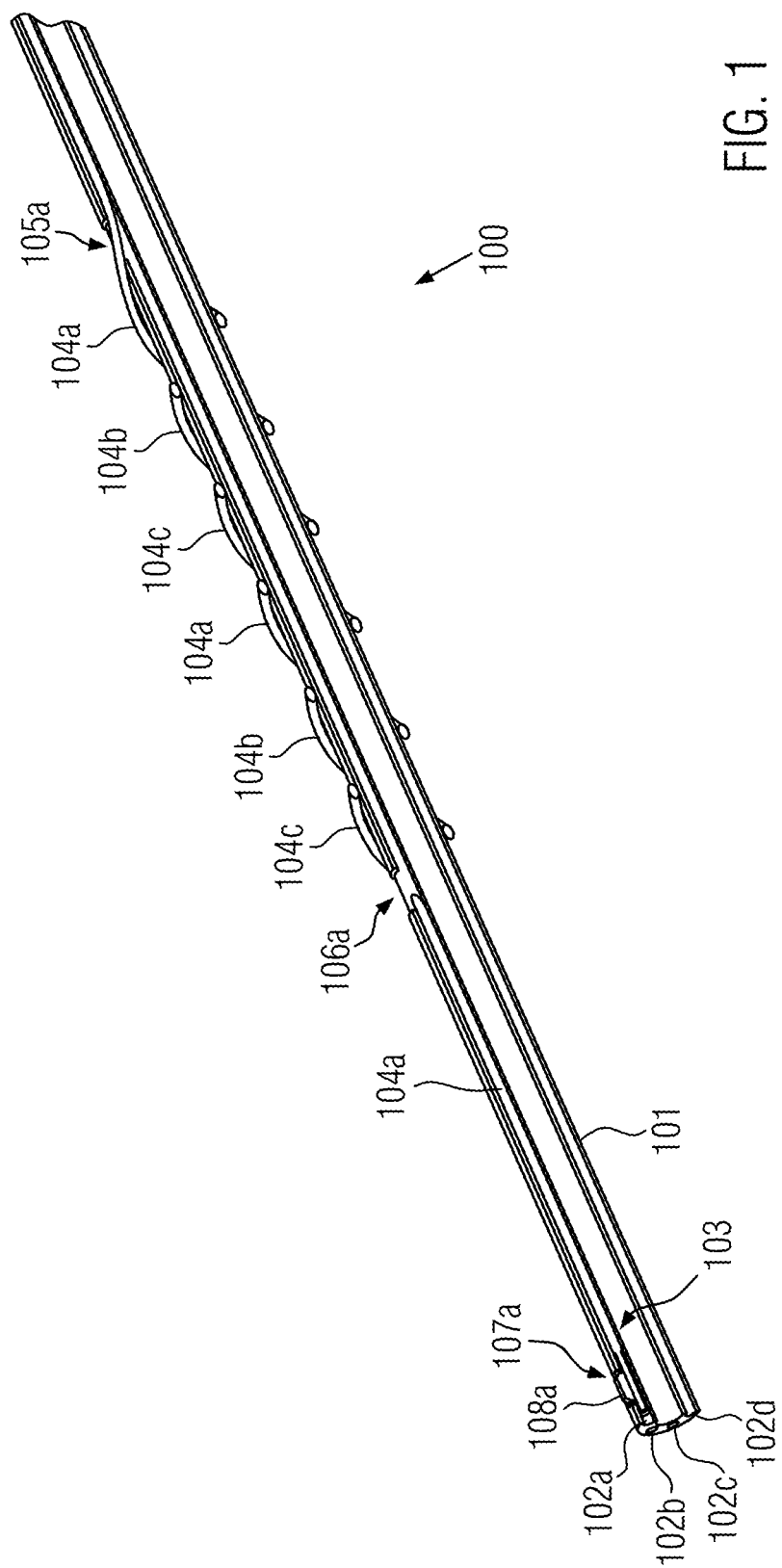
FIG. 1 illustrates a sectional view of a proximal portion of embodiments of an implantable lead.
Figure 2:
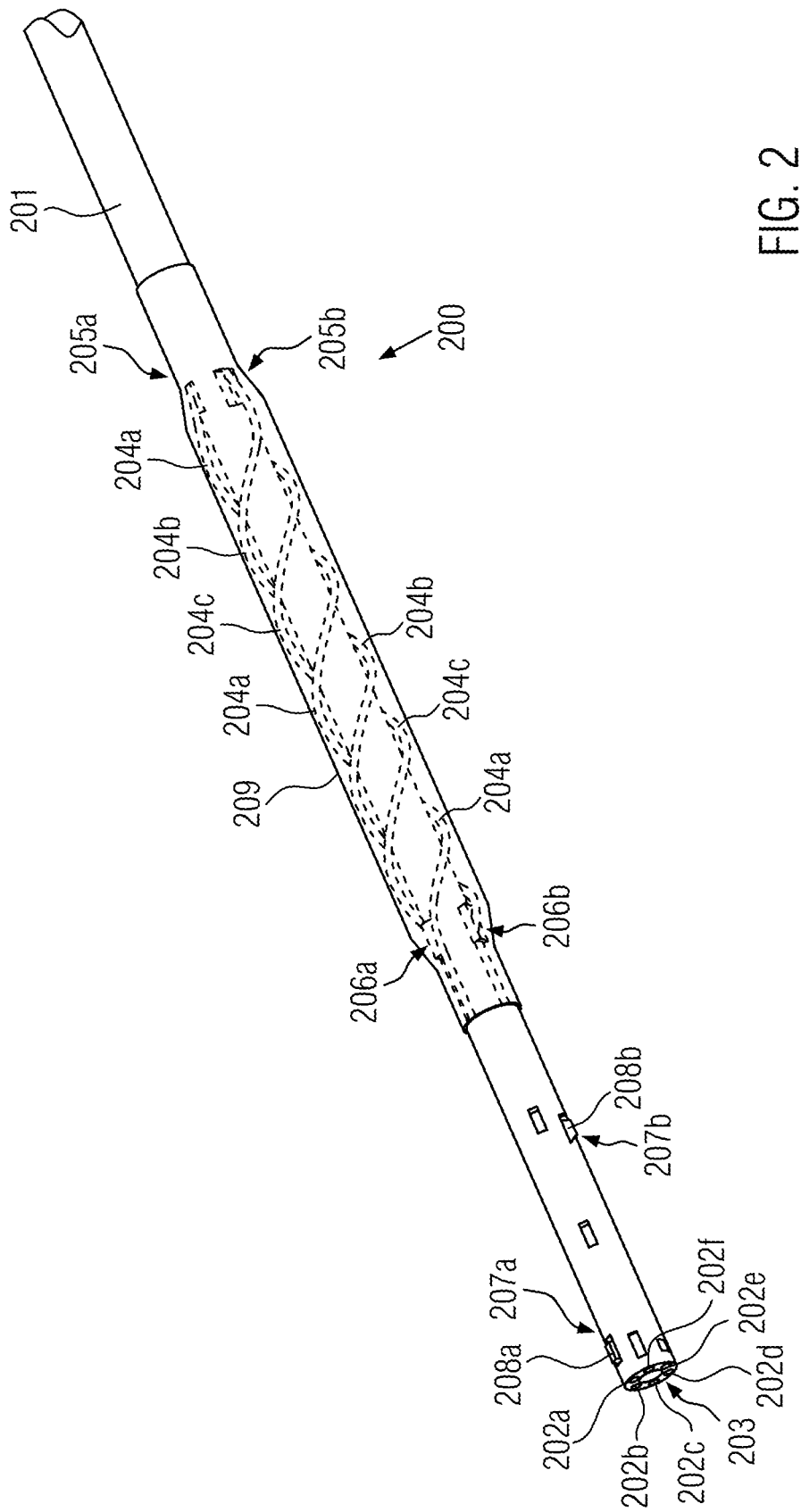
FIG. 2 illustrates a proximal portion of further embodiments of an implantable lead.
Figure 3:
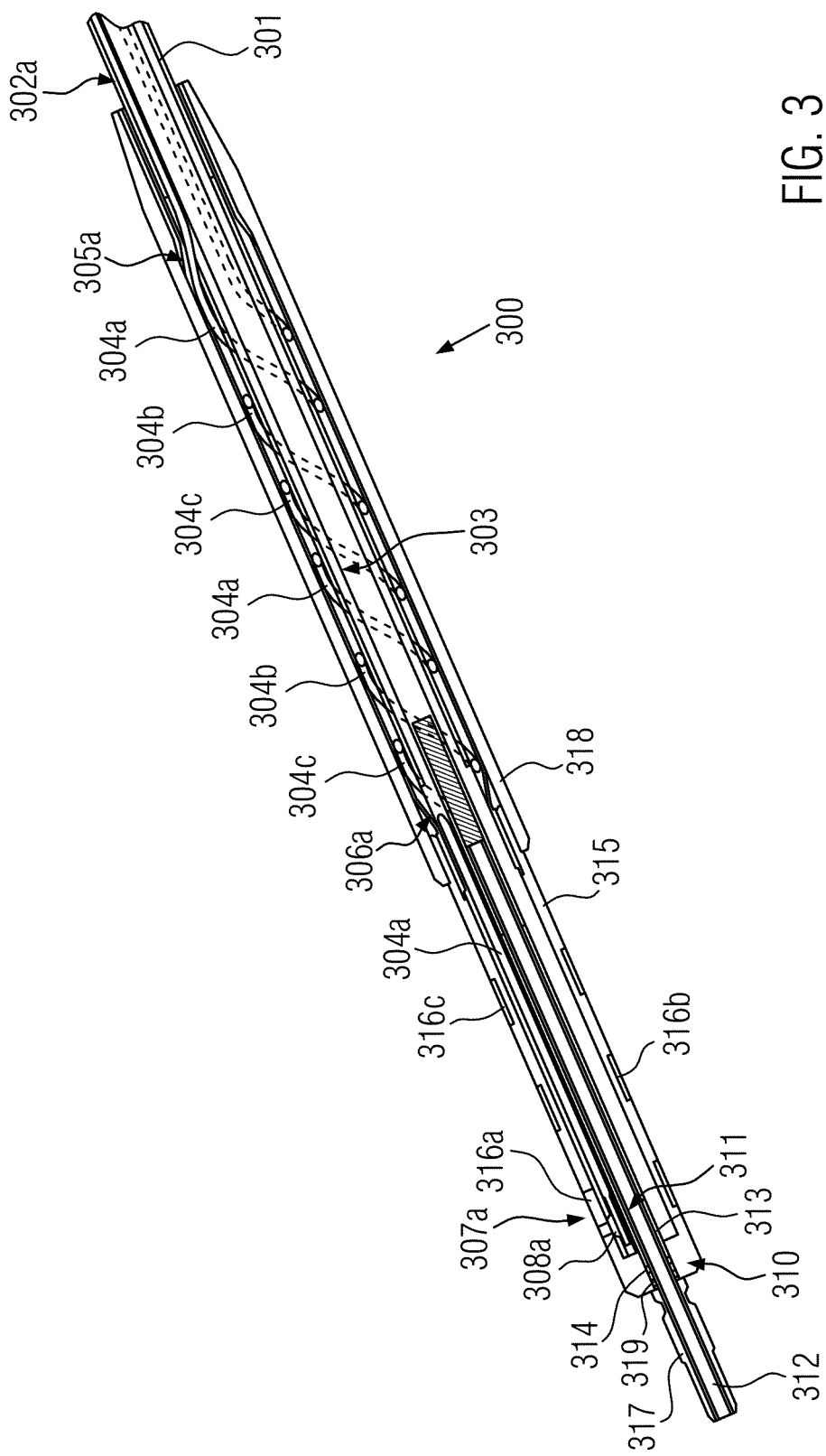
FIG. 3 illustrates another sectional view of a proximal portion of even further embodiments of an implantable lead.

The embodiments described hereafter with reference to FIGS. 1 to 3 relate to implantable leads 100, 200, 300 to be used with active implantable medical devices such as implantable pacemakers and/or defibrillators. In these embodiments, it is to be understood that the distal end of each one of the implantable leads 100, 200, 300 is configured for sensing and/or stimulating a tissue according to well-known configurations. In particular, it is to be understood that the respective distal end of the implantable leads 100, 200, 300 comprises at least one distal sensing and/or stimulating electrode (which can be a ring electrode, an emerging electrode, or the like) connected to a respective electrically conductive wire 104a, 204a, 304a that is arranged in the elongated body 101, 201, 301 and extends towards the proximal end of the respective implantable lead 100, 200, 300. The detailed description of the distal end of the implantable leads 100, 200, 300 will, therefore, be omitted for the sake of brevity, as it is already within the grasp of the skilled person in the field of implantable leads.

FIG. 1 illustrates a sectional view of a proximal portion of an implantable lead 100 according to embodiments of the present disclosure. As mentioned above, the implantable lead 100 comprises a body 101, which is elongated and can be essentially tubular. In this case, the lead body 101 has at least one lumen 102a extending therein. Without being restricted thereto, the lead body 101 may be made by extruding or molding a biocompatible, preferably flexible, material such as polyurethane.

As also mentioned above, the implantable lead 100 comprises at least one electrically conductive wire 104a extending in the lead body 101 from the distal end (not illustrated) towards the proximal end of the lead body 101, which is visible in the section of the implantable lead 100 illustrated in FIG. 1. In particular, in the visible section illustrated in FIG. 1, the electrically conductive wire 104a is accommodated in the lumen 102a up to a first opening or through hole 105a extending in the lead body 101 between its outer surface and the lumen 102a. The electrically conductive wire 104a may be further arranged according to the following configuration: the electrically conductive wire 104a exits lumen 102a via opening or through hole 105a and is then wound around the outer surface of the lead body 101 over a predefined portion, in other words it spirals around and along a portion of a predefined length of the lead body 101. Although the embodiment illustrated represents a proximal end portion of the lead body 101, as mentioned above, the predefined portion could be provided at any desired section of the lead body 101, for instance towards the distal end thereof, or in a middle section. In comparison with known configurations in which an electrically conductive wire extends within a lumen all the way from the distal end to the proximal end of a lead body, the advantageous configuration of the present disclosure described above and illustrated in FIG. 1 improves the flexibility and durability of the electrically conductive wire 104a with respect to mechanical stress, in particular bending stress, over the entire predefined portion. These advantages are reinforced by the various embodiments and variants described hereafter.

At the actual proximal end of the lead body 101, the electrically conductive wire 104a can be connected to a terminal end or an electrical contact 108a, which is needed for the electrical connectivity with the corresponding structures (e.g., socket) of the housing of an active implantable medical device (not illustrated). Without being restricted thereto, the electrical contact 108a can be provided as an emerging junction, along the lines of EP 1 641 084 B1, although other methods and/or techniques may be used. Thus, as can be seen in FIG. 1, in some embodiments, this can be achieved using an electrical contact 108a attached, for instance, by welding and/or crimping and/or gluing and/or any other known method, to the end of electrically conductive wire 104a, and emerging from the lead body 101, here from lumen 102a, through another proximal opening or through hole 107a, which is an opening or through hole arranged near the proximal end of the lead body 101. For standard connectivity requirements in the field of implantable leads, more than one such electrical contact 108a may have to be provided, depending on the number of electrically conductive wires and sensing and/or stimulating electrodes. For instance, for IS-4 or DF-4 standard connectors to be provided over the proximal end section of the lead body 101, three such electrical contacts 108a would be required, in which case they could be spaced apart or offset longitudinally and/or along a circumference of the lead body 101, preferably about 120° from one another.

Following further advantageous embodiments, also illustrated in FIG. 1, the lead body 101 can comprise at least one second opening or through hole 106a, provided at a predefined distance from the first opening or through hole 105a, hence different from the first through hole 105a, in particular in the longitudinal direction of the lead body 101 and, in this embodiment, closer to the proximal end than the first opening or through hole 105a. When an emerging junction is used as described above, the second opening or through hole 106a is different from the proximal opening or through hole 107a mentioned above. In particular, the second opening or through hole 106a can be provided between the first opening or through hole 105a and the proximal opening or through hole 107a, after a predefined distance from the first opening or through hole 105a along the lead body 101, so as to leave a predefined proximal end portion of the lead body 101, comprising the proximal opening or through hole 107a, to be used for connectivity purposes. However, as mentioned above, in other embodiments, the first through hole 105a and the second through hole 106a could be more towards the distal end of the lead body 101, or even towards a middle section thereof, and more than one predefined portions could be provided in different parts of the lead body 101. In any case, the predefined portion provided with improved flexibility and durability would then be the portion extending between a first through hole 105a and a corresponding second through hole 106a, in addition to being the portion over which the electrically conductive wire 104a is wound around the outer surface of the lead body 101.

The various through holes described here, whether the at least one first opening or through hole 105a, the at least one second opening or through hole 106a, or the proximal opening or through hole 107a, can be achieved for instance using laser ablation techniques, or any other known technique suitable for this purpose.

In any case, when at least one second opening or through hole 106a is provided as described above, the electrically conductive wire 104a could then be further arranged according to the following configuration: after being wound, or in other words after spiraling, around the outer surface of the lead body 101 over the length of the predefined portion, the electrically conductive wire 104a could then re-enter the lead body 101 via the second opening or through hole 106a to be accommodated in a lumen thereof. In the embodiments illustrated in FIG. 1, since the second opening or through hole 106a also extends also into lumen 102a, the electrically conductive wire 104a is arranged within the same lumen 102a on either side of the predefined portion. Accordingly, over the predefined portion, the electrically conductive wire 104a is arranged with an essentially spiraling configuration, in particular around the outer surface of the lead body 101, that provides it with more flexibility and durability with respect to mechanical stress, in particular bending stress, when compared to known configurations, or when compared to the sections on either side of the predefined portion where the electrically conductive wire 104a is arranged within lumen 102a.

Furthermore, in some embodiments, the electrically conductive wire 104a could be wound more than once around the lead body 101 over the length of the predefined portion. For instance, without being restricted thereto, the configuration of the electrically conductive wire 104a could be such that it would be spiraling between one and six times, with the various spires so defined being more or less close to one another depending on the desired degree of flexibility and/or durability with respect to mechanical stress. This could be adjusted for instance so that the spires defined by the spiraling configuration of electrically conductive wire 104a over the length of the predefined portion could be arranged evenly, in other words with a homogeneous step between successive spires. One way of achieving a homogeneous step could be pulling on either or both ends of the electrical conductive wire 104a during the assembly process. The natural rigidity of the electrically conductive wire 104a, which could be for instance a micro-cable or the like, would then provide the homogeneous step in the spiraling configuration.

In addition, the principles described above can be adapted to embodiments in which the lead body has only one main lumen or is of the multi-lumen type, and/or to embodiments in which a plurality of electrically conductive wires is used, whether the electrically conductive wires are all arranged within said one main lumen, or each one within a respective lumen in a multi-lumen lead body.

In some embodiments, the body of an implantable lead could be a tubular lead body comprising only one main lumen. In other embodiments, the lead body could be a multi-lumen tubular lead body, for instance as illustrated in FIG. 1, which represents the lead body 101 as having a main lumen 103, which can have a larger diameter, and at least one lumen 102a parallel to the main lumen 103, which can have a smaller respective diameter. In the sectional view of FIG. 1, four lumina 102a, 102b, 102c, 102d in addition to the main lumen 103 are illustrated, although the skilled person will appreciate that the number and actual arrangement of lumina in a multi-lumen lead body may differ from what is illustrated (more or less lumina, not necessarily evenly arranged around the main lumen) without diverging from the scope of the present disclosure. Furthermore, the main lumen 103 does not need to be centered on the main axis of the lead body 101 and could also be off-centered. It is also clear that a lumen does not need to run exactly along or parallel to the main longitudinal axis of a lead body.

In addition, an implantable lead could comprise more than one distal sensing and/or stimulating electrode connected to a respective proximal electrical contact via a respective electrically conductive wire, arranged within the same lumen or within a respective distinct lumen of the lead body. In the sectional view of FIG. 1, two electrically conductive wires 104b, 104c are illustrated in addition to the electrically conductive wire 104a described above, with analogous configurations, although the skilled person will appreciate that the number of electrically conductive wires may differ from what is illustrated without diverging from the scope of the present disclosure.

Thus, depending on embodiments, when the body of the implantable lead comprises only one main lumen, and one or more electrically conductive wires, it is possible to provide the predefined portion by means of at least one opening or through hole extending into said main lumen. In this case, one or more electrically conductive wires could be arranged with the configurations and variants thereof described above.

Furthermore, when the lead body is of the multi-lumen type, for instance, in variants of the embodiments illustrated in FIG. 1, the at least one electrically conductive wire 104a does not need to be arranged in the same lumen 102a on either side of the predefined portion, or in other words it does not need to re-enter the lead body 101 in the same lumen 102a via specifically the second opening or through hole 106a. For instance, other second openings or through holes (not visible in the sectional view of FIG. 1) could be provided towards the proximal end portion of the lead body 101, in particular, in an offset configuration with respect to the illustrated second opening or through hole 106a, whether longitudinally and/or along a circumference of the lead body 101, and extending into any other lumen of the multi-lumen lead body 101 than lumen 102a, for instance, extending in any of lumina 102b, 102c, 102d. In short, after exiting the distal section of the lead body 101 via the first through hole 105a and adopting the spiraling configuration described above along the predefined portion, the electrically conductive wire 104a could re-enter the lead body 101 into the same lumen 102a as described above, or into any other lumen 102b, 102c, 102d via a respective other opening or through hole in an analogous manner, or even if so desired into the main lumen 103, via a corresponding other opening or through hole.

Furthermore, as mentioned above, FIG. 1 focuses on a proximal end portion of implantable lead 100. In the illustrated embodiments, as can also be taken from the description above, the at least one first opening or through hole 105a is provided at a distal section of the illustrated proximal end portion. In turn, the at least one second opening or through hole 106a is provided between through hole 105a and proximal through hole 107a, the latter being in the vicinity of the actual proximal end of the lead body 101. Here, it will be appreciated that the positions of the first through hole 105a and second through hole 106a could be inverted, the first through hole 105a then being a "proximal" through hole and the second through hole 106a then being a "distal" through hole. In other words, the denominations of "first" through hole and "second" through hole are interchangeable without departing from the scope of this disclosure.

Furthermore, in embodiments where a plurality of electrically conductive wires 104a, 104b, 104c are used with a multi-lumen lead body 101 as described above, additional "first" openings or through holes can be provided in relation to the electrically conductive wires 104b, 104c in a similar manner to through hole 105a. In order to avoid creating a weakened section on the lead body 101, the other first openings or through holes can be spaced apart and/or offset longitudinally and/or along a circumference of the lead body 101, preferably by multiples of 60° with respect to through hole 105a and from one another.

Analogous spaced apart and/or offset arrangements could be used regarding additional "second" openings or through holes with respect to through hole 106a, and/or regarding any other necessary through hole, with the same advantages of avoiding to create a weakened section on the lead body 101. As can be taken from the disclosure above, the predefined portion would be the portion over which the various electrically conductive wires 104a, 104b, 104c are arranged in the configuration described above, in particular in the spiraling configuration, between a "first" and a "second" through hole. In the embodiment illustrated in FIG. 1, the length of the portion over which the flexibility and durability advantages are provided can extend essentially from the most distal of the "first" openings or through holes, which include through hole 105a, to the most proximal of the "second" openings or through holes, which include through hole 106a.

Furthermore, offsets along a circumference of the lead body 101 could also be advantageous in embodiments where the electrically conductive wires 104a, 104b, 104c would be arranged in a different respective lumen 102a, 102b, 102c, 102d on either side of the predefined portion.

As mentioned above, the features and advantages described above also apply for each electrically conductive wire in variants comprising more than one electrically conductive wire. In the embodiments illustrated in FIG. 1, the configurations and advantages described above apply to each one of the illustrated electrically conductive wires 104a, 104b, 104c.

FIGS. 2 and 3 illustrate a respective proximal portion of implantable leads 200, 300 according to further embodiments. The implantable leads 200, 300 both comprise all the features already described regarding the implantable lead 100 of the embodiments illustrated in FIG. 1. For the sake of brevity, it is therefore referred back to the disclosure above for details regarding features in common between the illustrated embodiments, advantages and further variants thereof.

Referring to FIG. 2, the implantable lead 200 comprises a lead body 201 of the multi-lumen type and comprises various inner lumina 202a, 202b, 202c, 202d, 202e, 202f arranged about a main lumen 203. Furthermore, a plurality of electrically conductive wires, here electrically conductive wires 204a, 204b, 204c, connects respective distal sensing and/or stimulating electrodes (not illustrated) to respective emerging electrical contacts, out of which at least electrical contacts 208a, 208b are visible emerging from respective proximal openings or through holes 207a, 207b.

As can also be seen in FIG. 2, each electrically conductive wire 204a, 204b, 204c coming from the distal end of the implantable lead 200 emerges or exits from a respective one among inner lumina 202a, 202b, 202c, 202d, 202e, 202f of the lead body 201 via a respective "first" opening or through hole, out of which at least through holes 205a, 205b can be distinguished. Each electrically conductive wire 204a, 204b, 204c is then arranged in the advantageous configuration described above, namely, essentially spiraling or wound around lead body 201 over a predefined portion towards the proximal end.

Furthermore, each electrically conductive wire 204a, 204b, 204c can then re-enter a respective inner lumen among lumina 202a, 202b, 202c, 202d, 202e, 202f via a respective "second" opening or through hole, out of which at least through holes 206a, 206b can be distinguished in FIG. 2.

In addition, following further embodiments, the implantable lead 200 of the embodiments illustrated in FIG. 2 can comprise an additional, optional, protective or reinforcing sleeve 209 arranged at least over the predefined portion of the lead body 201 having the electrically conductive wires 204a, 204b, 204c arranged in the spiraling configuration described above. The sleeve 209 is provided, in particular, also on the exposed portion of the electrically conductive wires 204a, 204b, 204c between the series of first openings or through holes 205a, 205b and the series of second openings or through holes 206a, 206b, thereby providing additional protection and stability, as well as durability, against mechanical stress, in particular bending stress, to this portion of the lead body 201.

Without being restricted to these materials, protective or reinforcing sleeve 209 can be made, preferably, of a biocompatible material such as polyurethane, silicon, or the like. In order to improve the protection provided by sleeve 209, during the assembly of the implantable lead 200, the sleeve 209 can be expanded, for instance chemically, and then arranged over the predefined portion comprising the exposed spiraling electrically conductive wires 204a, 204b, 204c. The evaporation of the solvent used for expanding the sleeve 209 can then allow a homogeneous retraction of the protective or reinforcing sleeve 209 over the exposed spiraling electrically conductive wires 204a, 204b, 204c, thereby maintaining the exposed part of the electrically conductive wires 204a, 204b, 204c. Thus, the protective or reinforcing sleeve 209 improves, even more, the mechanical protection of this sensitive area against mechanical stress, such as bending stress, during the implantation operation by a practitioner. The sleeve 209 also increases the mechanical protection against mechanical fatigue which can be due to a patient's movements over the lifetime of the implantable lead 200 once it has been implanted.

Regarding the embodiments illustrated in FIG. 3, the implantable lead 300 essentially comprises all the features described in the embodiments illustrated with FIG. 2. In particular, the implantable lead 300 also comprises a multi-lumen lead body 301 of the multi-lumen type and comprises various inner lumina (most of which are not visible in the sectional view of FIG. 3), out of which at least lumen 302a can be distinguished, which are arranged about a main lumen 303. Furthermore, a plurality of electrically conductive wires, here electrically conductive wires 304a, 304b, 304c, connects respective distal sensing and/or stimulating electrodes (not illustrated) to respective emerging electrical contacts, out of which at least electrical contact 308a is visible emerging from a respective proximal opening or through hole 307a.

As also illustrated in FIG. 3, following some of the embodiments described above, each electrically conductive wire 304a, 304b, 304c coming from the distal end of the implantable lead 300 emerges or exits from a respective one among the various inner lumina of the lead body 301 via a respective "first" opening or through hole, out of which at least through hole 305a is indicated. Each electrically conductive wire 304a, 304b, 304c is also arranged in the advantageous configuration described above, namely essentially spiraling or wound around lead body 301 over a predefined portion in direction of the proximal end from the respective first opening or through hole. Each electrically conductive wire 304a, 304b, 304c can then re-enter a respective inner lumen among the plurality of lumina of the multi-lumen lead body 301 via a respective "second" opening or through hole, out of which at least through hole 306a is indicated.

Following further embodiments, the implantable lead 300 can optionally also comprise an electrical connector plug, which can be configured following a particular desired connectivity standard, such as IS-4, DF-4, or the like. In the embodiments illustrated in FIG. 3, the implantable lead 300 can comprise an electrical connector cap 310 and a contact pin assembly 311, both of which will be described hereafter.

As can be taken from FIG. 3, the contact pin assembly 311 can comprise an axial contact pin 312, partly accommodated in the main lumen 303 of the lead body 301, and partly protruding from the proximal end of the lead body 301. If so desired, the part of the axial contact pin 312 accommodated in the main lumen 303 can be covered by an insulating sleeve 313, preferably of biocompatible material, and the contact pin assembly 311 can also comprise further elements such as a one or more optional stop rings 314, and one or more optional seal rings 319, along the axial contact pin 312. In some embodiments, an optional internal coil with a fastening mechanism, such as a screw (not illustrated), can be provided within the implantable lead 300, in particular through the main lumen 303 and/or the axial contact pin 312, which can then be preferably tubular. The axial contact pin 312 can then preferably be rotatable with respect to the lead body 301, and more preferably also with respect to the electrical connector cap 310. Furthermore, the axial contact pin 312 can also be connected to a distal sensing and/or stimulating electrode via an electrically conductive wire.

Furthermore, the electrical connector cap 310 can comprise a tubular body 315, and a series of electrically conductive contact ports corresponding at least to some of the electrical lines to be connected to the distal sensing and/or stimulating electrodes. Here, a one piece tubular body 315 is illustrated. In preferred embodiments, the tubular body can be made of an insulating biocompatible material. Furthermore, in the embodiments illustrated in FIG. 3, the electrical connector cap 310 comprises three ring-shaped contact ports 316a, 316b, 316c provided around tubular body 315 and to be connected to a respective one of the three electrically conductive wires 304a, 304b, 304c. To this purpose, each contact ports 316a, 316b, 316c can have a protrusion that extends through the tubular body 315, and the respective inner protrusions can be offset with respect to one another along a circumference of the tubular body 315 so as to match the circumferentially offset electrical contacts emerging from the lead body 301.

Thus, as illustrated in FIG. 3, when the electrical connector cap 310 is mounted over the proximal end portion of the lead body 301 following the predefined portion with the spiraling electrically conductive wires 304a, 304b, 304c, a protrusion of each contact port 316a, 316b, 316c extending through the tubular body 315 into its main lumen will be positioned in front of a respective proximal electrical contact emerging from the lead body 301. In FIG. 3, this can be seen at the level of the emerging proximal electrical contact 308a which is essentially in contact with the inner protrusion of contact port 316a. It is then possible to secure the electrical connector cap 310 to the lead body 301, which is facilitated when the inner protrusion of each contact port 316a, 316b, 316c is provided with a through hole, by means of which each contact port 316, 316, 316 can be attached to an underlying emerging proximal electrical contact such as emerging electrical contact 308a, in particular, but not limited thereto, using laser welding techniques. It is optionally also possible to further attach and insulate the electrical connector cap 310 to the lead body 301, for instance by injecting an adhesive through one or more other through holes provided in the lead body 301 and/or in the tubular body 315, so as to fill any space or volume therebetween.

When the implantable lead 300 comprises a protective or reinforcing sleeve like the protecting or reinforcing sleeve 209 described with reference to FIG. 2, the protective or reinforcing sleeve can extend more than the predefined portion in the proximal and/or distal directions of the lead body 301, which is also the case of the sleeve 209 illustrated in FIG. 2. In this way, a distal end portion of the electrical connector cap 310 can end up covering a part of the protective sleeve immediately after the predefined portion with the spiraling electrically conductive wires 304a, 304b, 304c.

As further illustrated in FIG. 3, when the electrical connector cap 310 is positioned over the proximal end portion of the lead body 301 and fixed thereto, a part of the axial contact pin 312 of the contact pin assembly 311 can also protrude through the proximal end of the tubular body 315. This protruding part of the axial contact pin 312 can then be configured so that the electrical connector cap 310 and the pin assembly 311 correspond to a specific connectivity standard. To this purpose, a terminal end 317 configured for the desired specific standard, for instance IS-4 or DF-4 standards, can be provided over the protruding part of the axial contact pin 312 at the proximal end of the implantable lead 300. For instance, it could be attached using known welding techniques, or the like. In the embodiments illustrated in FIG. 3, the implantable lead 300, the electrical connector cap 310, and the pin assembly 311, in particular terminal end 317, are configured following the DF-4 standard. Here, it is understood that other embodiments with could relate to different types of standard connectors without diverging from the scope of the present disclosure.

Furthermore, as also illustrated in FIG. 3, the implantable lead 300 can comprise an optional insulating sleeve 318, which can be slid over the lead body 301, in particular, covering at least the predefined portion with the exposed spiraling electrically conductive wires 304a, 304b, 304c and, when applicable, also covering a protective or reinforcing sleeve like the sleeve 209 described in relation to FIG. 2. Optionally, the insulating sleeve 318 can also cover a rear or distal portion of the electrical connector cap 310 and be mechanically fixed thereto, for instance by clipping into holes provided for this purpose at the distal portion of the connector cap 310. In this way, it is possible to further reinforce the portion with the spiraling electrically conductive wires 304a, 304b, 304c, while also preventing body fluids from penetrating, in particular filtering, into the distal portion of the electrical connector cap 310. The insulating sleeve 318 can be made of silicon or any other suitable flexible biocompatible material.

In short, the present disclosure provides an implantable lead having a predefined portion along which one or more electrically conductive wires are arranged with a configuration that results in various degrees of improved mechanical stability and durability against mechanical stress, in particular bending stress, in comparison to known implantable leads.

In some embodiments, the present disclosure provides said predefined portion immediately following the electrical connector portion of the implantable lead, which is the portion known to be subject to intense mechanical stress, in particular bending stress, during the implantation operation, as well as over the lifetime of the lead once it has been implanted.

The invention claimed is:

1. An implantable lead comprising:
   an elongated lead body comprising a central lumen and a plurality of lumina having a smaller diameter than the central lumen, the plurality of lumina positioned around the circumference of the central lumen and extending in a direction parallel to the central lumen, each of the plurality of lumina comprising at least one through hole; and
   at least one electrically conductive wire;
      wherein, for a first lumina of the plurality of lumina, a first through hole extends from an outer surface of the lead body into said first lumina, and the at least one electrically conductive wire is arranged in said first lumina at least on one side of said first through hole;
      wherein said electrically conductive wire is further arranged in a configuration exiting the first lumina via said first through hole and wound around a predefined portion of the outer surface of the lead body;
      wherein the lead body has a proximal end portion comprising an electrical connector configured for connecting the implantable lead to a housing of an active medical implantable device and a distal end potion configured for sensing and/or stimulating a tissue; and
      wherein said first through hole and said predefined portion is arranged closer to the proximal end portion than to the distal end portion, the predefined portion immediately following the electrical connector.

2. The implantable lead according to claim 1, wherein a second through hole, different from the first through hole, extends from the outer surface of the lead body into the first lumina, and wherein said electrically conductive wire is further arranged in a configuration entering the first lumina via said second through hole.

3. The implantable lead according to claim 2, wherein said first through hole and said second through hole extend into the same lumina of the plurality of lumina, whereby said electrically conductive wire is arranged within the first lumina on either side of the predefined portion.

4. The implantable lead according to claim 1, wherein the plurality of lumina comprise at least two lumina, and wherein a second through hole extends into a second lumina of the plurality of lumina, whereby said electrically conductive wire is arranged within a different one of the plurality of lumina on either side of the predefined portion.

5. The implantable lead according to claim 1, wherein said first through hole and a second through hole are spaced apart in a longitudinal direction of the elongated lead body.

6. The implantable lead according to claim 1, wherein first through hole and a second through hole are offset with respect to each other in a circumferential direction of the elongated lead body.

7. The implantable lead according to claim 1, wherein said at least one electrically conductive wire is further arranged in a configuration wound at least once around the predefined portion of the outer surface of the lead body.

8. The implantable lead according to claim 1, wherein said at least one electrically conductive wire is a micro-cable.

9. The implantable lead according to claim 2, wherein said second through hole is arranged closer to the proximal end portion than to the distal end portion.

10. The implantable lead according to claim 1, further comprising at least one protective sleeve arranged over the lead body and extending at least over the predefined portion.

11. The implantable lead according to claim 10, wherein a distal end portion of an electrical connector plug is arranged over a proximal end portion of the protective sleeve, whereby a portion of the protective sleeve is left uncovered by the electrical connector plug.

12. The implantable lead according to claim 11, further comprising an insulating sleeve arranged over the lead body and extending at least over the predefined portion, wherein the insulating sleeve extends at least over the protective sleeve.

13. The implantable lead according to claim 12, wherein the protective sleeve and/or the insulating sleeve is/are made of a flexible biocompatible material.

14. The implantable lead according to claim 6, wherein the first and second through holes are offset by 60° intervals or a multiple thereof.

15. The implantable lead according to claim 7, wherein the electrically conductive wire is wound between one and six times around the predefined portion of the outer surface of the lead body.

16. The implantable lead according to claim 12, wherein the insulating sleeve extends over the distal end portion of the electrical connector plug and at least over the uncovered portion of the protective sleeve.

17. The implantable lead according to claim 1, wherein the plurality of lumina includes at least four lumina and wherein the at least one conductive wire includes at least four conductive wires.

18. The implantable lead according to claim 17, wherein each of the at least four conductive wires are arranged in a respective one of the at least four lumina.

\* \* \* \* \*